US005807686A

United States Patent [19]
Wagner et al.

[11] Patent Number: 5,807,686
[45] Date of Patent: Sep. 15, 1998

[54] PLURIPOTENTIAL QUIESCENT STEM CELL POPULATION

[75] Inventors: John E. Wagner, Plymouth, Minn.; Jane S. Lebkowski, Portola Valley, Calif.

[73] Assignees: Regents of University of Minnesota, Minneapolis, Minn.; Rhone-Poulenc Rorer Pharmaceuticals, Collegeville, Pa.

[21] Appl. No.: 482,318

[22] Filed: Jun. 6, 1995

Related U.S. Application Data

[63] Continuation of Ser. No. 976,927, Nov. 16, 1992, abandoned.

[51] Int. Cl.$^6$ .................. G01N 33/53; G01N 33/567; C12N 5/00; C12N 15/00
[52] U.S. Cl. ............. 435/7.1; 435/7.21; 435/240.1; 435/172.3; 424/93.21
[58] Field of Search ................ 435/240.2, 7.21, 435/240.1; 424/93.1

[56] References Cited

U.S. PATENT DOCUMENTS

| | | | |
|---|---|---|---|
| 4,489,710 | 12/1984 | Spitler | 424/25 |
| 5,061,620 | 10/1991 | Tsukamoto | 435/7.21 |

FOREIGN PATENT DOCUMENTS

| | | | |
|---|---|---|---|
| 455482 | 11/1991 | European Pat. Off. | |
| 0455482A3 | 6/1994 | European Pat. Off. | C12N 5/08 |

OTHER PUBLICATIONS

Goldstein, in *The Lectis*, Chapter 2, p. 155, Edited by Liener, Sharon and Goldstein, 1986.
Visser et al J Exp. Med. 59: 1576, 1984.
Jones et al. Nature 347: 188, 1990.
Boggs et al. Int. J. Cell Cloning 8: 80, 1990.
Brandt et al J. Clinical Invest 82: 1017, 1988.
Andrews et al J Exp. Med 172: 355, 1990.
Visser et al., "Isolation of murine pluripotent hemopoietic stem cells" *J. Exp. Med.* (1984) 59:1576–1590.
Jones et al., "Separation of pluripotent haematopoietic stem cells form spleen colony–forming cells" *Nature* (1990) 347:188–189.
Wagner et al., "Separation of primitive human hematopoietic stem cells from committed progenitors by counterflow elutriation (CE) followed by a soybean agglutinin negative depletion and CD34 positive selection" *Blood* (1991) 78:403a (abstract No. 1603).
Boggs et al Int J. Cell Cloning 8: 80, 1990.
Wagner et al (Abstract D211), J. Cell. Biochem Supp 16 A, 1992.
Brandt et al J Clin Invest 82: 1017, 1988.
Jones et al Nature 347: 188, 1990.
Wagner et al Blood 78: 403a, 1991 (Abst 1603).

*Primary Examiner*—Suzanne E. Ziska
*Attorney, Agent, or Firm*—Morrison & Foerster

[57] ABSTRACT

A cell population which is composed of cells bearing the stem cell marker CD34 and which are small in size and have little granulation are obtained by separating low density mononuclear hematopoietic cells according to size and then selecting for CD34$^+$ cells in the smallest size fraction. The size of the cell population corresponds to that obtained at a flow rate of 25–29 ml/min in a counterflow elutriation method using a rotor equivalent to Beckman JE 5.0 spun at 900×g. This population of cells consists essentially of very early progenitor cells and the cells are useful in autologous bone marrow transplantation as well as gene therapy.

8 Claims, 4 Drawing Sheets

PLURIPOTENTIAL QUIESCENT STEM CELL POPULATION

This is a continuation of application Ser. No. 07/976,927 filed Nov. 16, 1992, now abandoned.

TECHNICAL FIELD

The invention is related to the field of cell sorting and cell subpopulations. More precisely, the invention concerns a stem cell population which is pluripotential and relatively quiescent.

BACKGROUND ART

Stem cells are thought to be manufactured in the adult bone marrow as relatively undifferentiated progenitors for a variety of blood cells including erythrocytes, lymphocytes, and polynuclear cells. Stem cells are also present in the peripheral blood and in umbilical cord blood. It is believed that at some point in their development and differentiation, individual cells become committed to a particular cellular goal. Thus, the population of stem cells found in the bone marrow of a subject at any one time will contain stem cells in various stages of differentiation and development.

In murine models, this hematopoietic system has been divided into three functionally distinct subpopulations: the youngest is an uncommitted pluripotential stem cell population capable of self-renewal and further differentiation; these differentiate further into a committed multipotential progenitor population; these, then, finally become committed unipotential progenitors. All of these stem cell populations express the CD34 antigen in the human system, and it appears CD34 expression decreases with differentiation.

Attempts have been made in the past to obtain a subset of the total stem cell population which is uncommitted, and thus provides the most versatile population for engraftment and has the best potential for genetic modification in gene therapy. U.S. Pat. No. 5,061,620 to SyStemix utilizes cell surface markers to provide a defined subpopulation in human stem cells. Murine subpopulations have also been isolated by the removal of lineage-committed cells followed by positive selection for cells bearing the Thy-$1^{low}$, the stem cell antigen (Sca-1) and the wheat germ agglutinin (WGA)$^+$ phenotype (Visser et al., *J Exp Med* (1984) 59:1576). Murine stem cells have also been separated based on size to obtain pluripotential cells relatively free of multipotent progenitors (Jones, et al., *Nature* (1990) 347:188–189).

Each of the foregoing separation methods yields a subpopulation with particular characteristics; it is not certain that all of these characteristics are desirable for use in engraftment or in gene therapy.

It has now been found that a subset of human stem cells can be obtained by subjecting low density mononuclear bone marrow cells (or other sources of stem cells) to counterflow elutriation and then recovering CD34$^+$ cells from the fractions containing the cells of smallest size. This subpopulation has the characteristics expected for a very primitive stem cell, and could be particularly useful in transplantation and gene therapy.

An abstract describing the results of counterflow elutriation followed by CD34$^+$ segregation of human low-density mononuclear bone marrow cells was published in 1991. (Wagner, et al, 78:10 *Blood* suppl. 1, 403a, abstract 1603, 1991).

DISCLOSURE OF THE INVENTION

The invention provides a subpopulation of human stem cells that are quiescent and pluripotent. These cells are those of small dimension that have CD34$^+$ markers on their surfaces. This population is depleted in cells which express CD33, CD38, HLA/DR, CD19 and CD3. These cells also have a high density of MIP1α, stem cell factor (SCF), IL-6, IL-3, IL-1α, and G-CSF receptors.

Thus, in one aspect, the invention is directed to a population of human hematopoietic stem cells consisting of mononuclear low density hematopoietic cells which correspond in size to those in flow rate fractions of 25–29 ml/min in a rotor of size equivalent to Beckman JE 5.0, spun at 900×g, and which are CD34$^+$. In short-term bone marrow cultures, these cells do not provide CFU-GM, BFU-E, or CFU-GEMM. More than 90% of this population contains receptors for SCF and MIP-1α, but the population does not proliferate in standard long-term bone marrow culture in the presence or absence of SCF. However, under appropriate conditions the cells are capable of proliferation ex vivo.

In other aspects, the invention is directed to methods to obtain the cell population of the invention and to methods of using this population.

MODES OF CARRYING OUT THE INVENTION

Figure 1A:
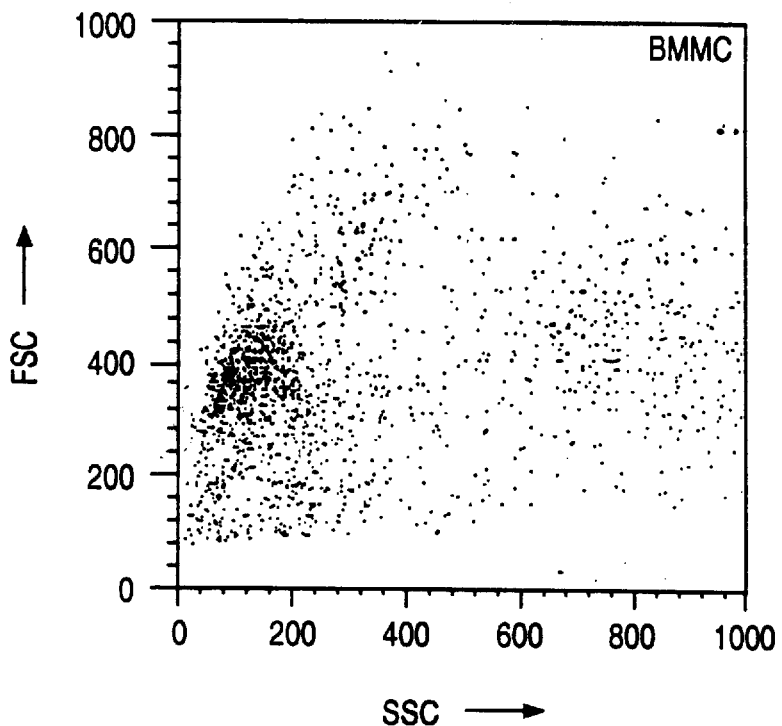
FIGS. 1A–1D show the distribution of CD34$^+$ cells in various fractions from counterflow elutriation.

The invention provides a population of cells that could be particularly useful in gene therapy and in transplantation. The cells appear to be extremely primitive. They are collectively characterized by a typical surface ligand expression pattern and are collectively positive or negative for these markers. Specifically, this population is depleted in cells which express CD33, CD38, HLA/DR, CD19 and CD3, but have a high density of MIP1α, stem cell factor (SCF), IL-6, IL-3, IL-1α, and GM-CSF receptors.

The population is conveniently prepared by an initial size separation of the low density mononuclear fraction of bone marrow cells so that cells are recovered which are agranular and small and have 0–1 nucleoli. This population is equivalent in size to that obtained in counterflow elutriation as described below in the fraction representing a flow rate of 25 to 29 ml/minute (FR $^{25}/_{29}$) when the separation is conducted with a Beckman JE 5.0 rotor at 900×g. The examples below illustrate the recovery of cells of this size using a specific counterflow elutriation (CE) procedure. However, any method for separating cells according to size can be used to collect an equivalent fraction (i.e., density gradient sedimentation could be substituted).

This subpopulation of appropriate size distribution is then subjected to further fractionation in two steps, one of which is optional. An optional step comprises treating the population with a solid support to which soybean agglutinin has been bound as an affinity ligand. The nonadherent cells are recovered. Typically, the contact is conducted at room temperature for about 1 hour on a nonvibrating surface. Appropriate solid supports coupled to soybean agglutinin may be obtained from Applied Immune Sciences, Menlo Park, Calif.

The nonadherent fraction of the cells contacted with the soybean agglutinin-derivatized support or the initial FR $^{25}/_{29}$ cells from size separation are then contacted with a solid phase substrate to which has been bound a ligand specifically reactive with the CD34 marker. Supports derivatized with, for example, antibodies or fragments thereof specific for CD34 may be obtained by methods known in the art and are commercially available from, for example, Applied Immune Sciences, Menlo Park, Calif. The supports are treated with the small cellular fraction under conditions wherein cells containing CD34 markers adhere to the support. Typically, incubation is conducted at room temperature for 1 hour to several hours on a nonvibrating surface. Nonadherent cells are removed, the surface washed if desired, and adherent cells are then recovered. The recovered cells constitute the quiescent pluripotential cell population of the invention.

The two or three steps involved in the fractionation of low density mononuclear bone marrow cells to obtain the desired cell population are most conveniently conducted in the order described above; however, there is no theoretical reason why the order cannot be altered. It is most convenient, however, to minimize the number of cells subjected to contact with affinity ligand-derivatized solid supports in view of the expense of preparing such supports and of the ligands themselves.

Figure 1B:
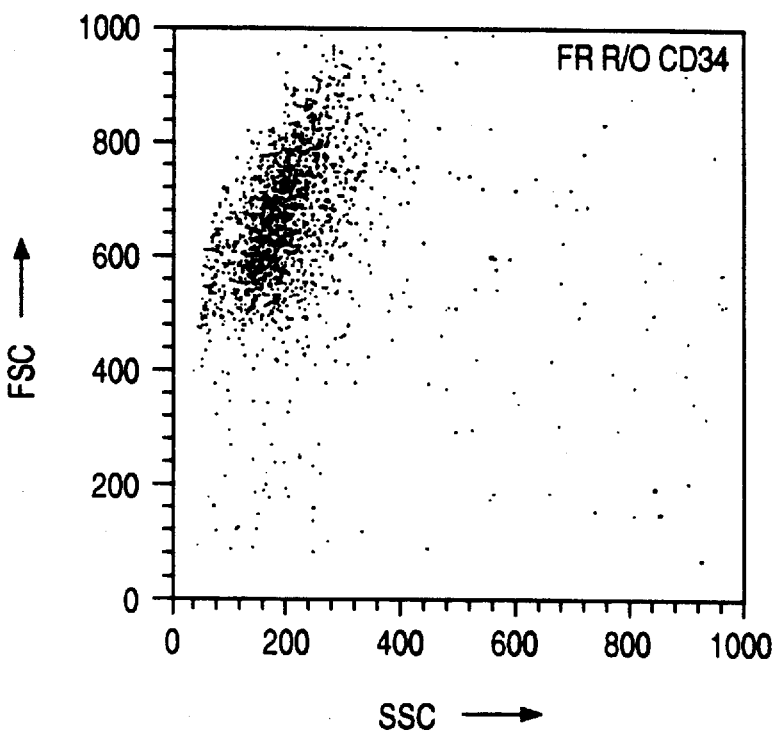
Figure 1C:
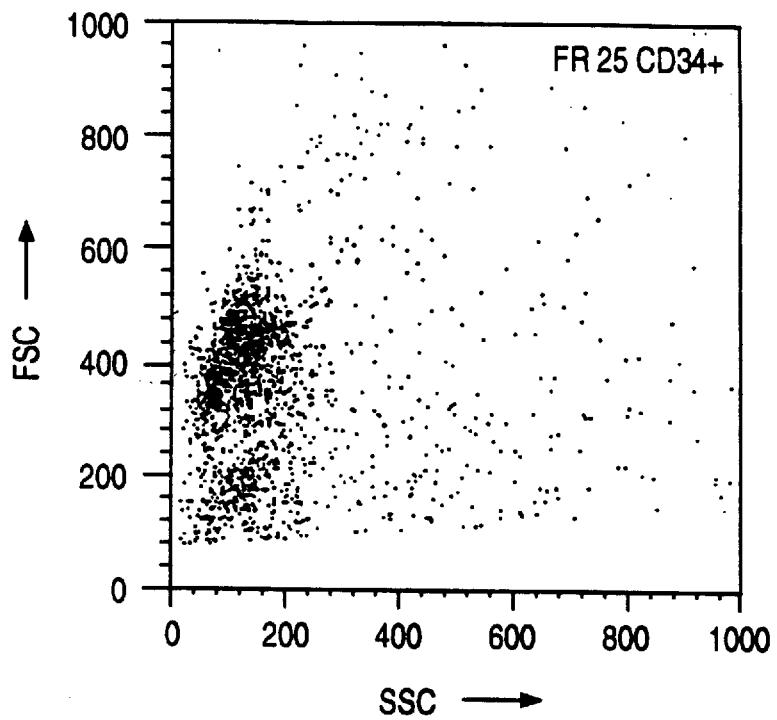
Figure 1D:
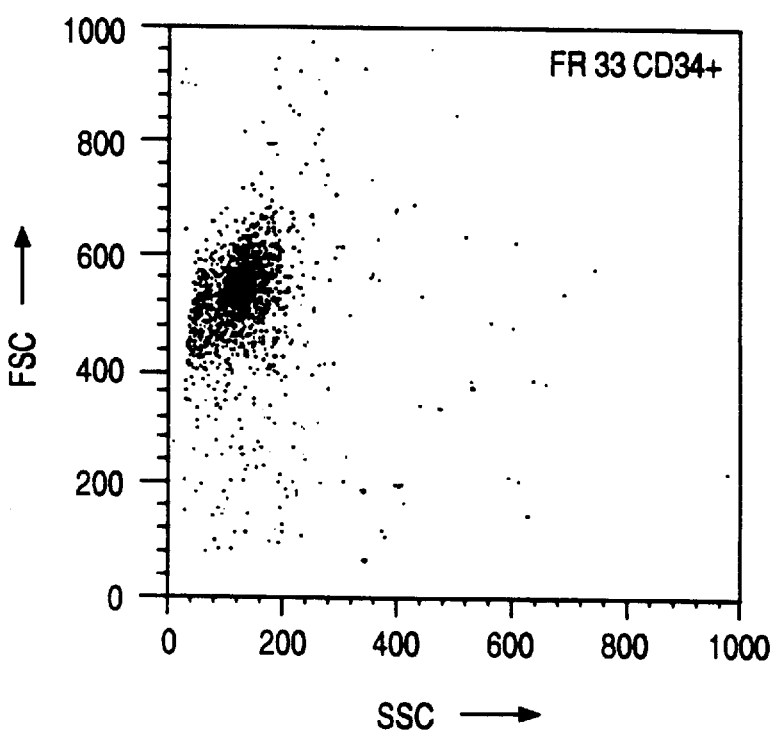

The population of CD34$^+$ cells obtained is characterized by its small size. A typical size distribution is shown in FIG. 1, further described in Example 1 below. As shown, CD34$^+$ cells are distributed over a large range of granularities (X-axis) and sizes (Y-axis) in the original bone marrow (FIG. 1A). However, the FR $^{25}/_{29}$ fraction contains CD34$^+$ cells of only smaller size and less granulation (FIG. 1C). The CD34$^+$ cells of FR $^{33}/_{37}$ (collected at flow rates of 33–37 ml/min) and RO (rotor off) fractions are larger (FIGS. 1D and 1B).

The cells of the FR $^{25}/_{29}$ CD34$^+$ population also contain high densities of MIP1$\alpha$ and SCF surface receptors, which are thought to characterize primitive cells and to provide a mechanism for suppressing proliferation. The cells of the invention could thus be cultured under conditions wherein the MIP1$\alpha$ receptors are blocked. Addition of SCF may also encourage growth, along with the other growth factors which have receptors on these cells.

Other characteristics of the cell population of the invention include their quiescent nature in the absence of such interference with MIP1$\alpha$ receptors, both in short-term and long-term bone marrow cultures, under standard conditions. Thus, without such adjustment they do not provide positive results in CFU-GM, BFU-E or CFU-GEMM assays. They are also characterized by typical surface marker patterns, including depletion in CD33, CD38, HLA/DR, CD19 and CD3. By depletion is meant that the density of markers in this population of cells is at least 3-fold less, preferably 5-fold less, and most preferably 10-fold less than the total CD34$^+$ cell population of the low-density mononuclear hematopoietic cells from which they are derived.

On the other hand, they have enhanced expression of MIP$\alpha$ and SCF receptors, as stated above, as well as receptors for IL-6, IL-3 and GM-CSF. By enhanced expression is meant that the density of markers in this population of cells is at least 3-fold more, preferably 5-fold more, and most preferably 10-fold more than the total CD34$^+$ cell population of the low-density mononuclear hematopoietic cells from which they are derived.

The population of cells having the characteristics described above is useful in effecting cell transplantation into subjects in need of such cell transplants. The cells may be used per se, for example, in protocols involving autologous transplants to replenish the stem cells of a subject suffering depletion through treatments such as chemotherapy or radiation therapy. The cells may also be genetically modified through, for example, homologous recombination or retroviral infection to remedy gene defects or to provide recombinant expression of desired proteins and administered to a subject in genetically modified form. Techniques for administration of such cells are commonly practiced using conventional methods known in the art.

The following examples are intended to illustrate, but not to limit, the invention.

EXAMPLE 1

Preparation of Uncommitted Stem Cells

Bone marrow samples were aspirated in small volumes from the posterior iliac crest of 22 healthy adult volunteer donors. Informed consent was obtained following the guidelines approved by the Committee on the Use of Human Subjects at the University of Minnesota.

Low density bone marrow mononuclear cells were isolated using Histopaque-1077 (Sigma Chemical Co., St. Louis, Mo.) and density gradient centrifugation (400×g for 45 minutes), washed twice with RPMI-1640 (Gibco, Grand Island, N.Y.) and resuspended in 10 ml of elutriation media.

For counterflow elutriation (CE), the washed low density mononuclear cells (2.7–7.8×10$^8$) were injected via a sampling site coupler into the inlet stream of a Beckman J6M/E centrifuge (Spinco Division, Beckman Instruments, Palo Alto, Calif.) equipped with a JE-5.0 rotor and standard chamber. One peristaltic pump (Masterflex, Cole Palmer Instruments, Chicago, Ill.) provided continuous flow of elutriation medium, which was 0.9% normal saline solution with 100 mg/dl D-glucose, 0.3 Mm disodium ethylenediaminetetraacetic acid (EDTA) and 50 mg/dl bovine serum albumin (BSA, Boehringer Mannheim, FRG), Ph adjusted to 7.20. The medium was sterilized prior to use.

Cells were delivered at a total flow rate of 15 ml/min (FR 15), rotor speed of 900×g and a temperature of 25° C. After 100 ml of eluate were collected, the flow rate was increased to 25 ml/min (FR 25). With the rotor speed held constant, the flow rates were sequentially increased to 29 ml/min (FR 29), 33 ml/min (FR 33), and 37 ml/min (FR 37), collecting 200 ml with each increment. The cells that remained in the chamber were captured by turning the rotor off (R/O fraction) and flushing the chamber with 100 ml of elutriation media. Each cell fraction was washed and centrifuged at 300×g for 10 minutes.

FRs 25 and 29 (FR $^{25}/_{29}$) and Frs 33 and 37 (FR $^{33}/_{37}$) were then combined. Viability was determined by trypan blue dye exclusion and cell recoveries were determined with a ZBI Coulter counter (Coulter Electronics, Hialeah, Fla.).

Each of the FR $^{25}/_{29}$, FR $^{33}/_{37}$ and R/O fractions was washed with elutriation medium and resuspended in 1 mM Dulbecco's Phosphate Buffer (DPBS) with 0.1 mM EDTA and 0.5% Gammimune (Miles Laboratory, Eickert, Ind.) for a 30 minute incubation. Cells from each fraction were loaded onto AIS T-25 MicroCELLector devices (Applied Immune Sciences, Menlo Park, Calif.) covalently coated with soybean agglutinin at a density of 2.0×10$^7$ target cells/flask and incubated for one hour at room temperature on a nonvibrating surface. The nonadherent cells were collected and the flasks were washed twice to remove all nonadherent cells from the flask surface.

1.5×10$^7$ cells from each fraction were loaded onto individual AIS T-25 MicroCELLector devices covalently coated with ICH3 (anti-CD34) and incubated for one hour at room temperature on a nonvibrating surface. The nonadherent cells were collected and the flasks were washed twice to remove all nonadherent cells. The adherent cells were collected by adding DPBS+10% fetal bovine serum (FBS, Hyclone) and hitting the flask firmly. The resulting populations were designated FR $^{25}/_{29}$ CD34$^+$, FR $^{33}/_{37}$ CD34$^+$, and R/O CD34$^+$.

The cells obtained in the fraction FR $^{25}/_{29}$ had cell diameters in a range of 8.0 to 9.4 microns; the majority of the cells had diameters that fell within a range of 8.0 to 8.5 microns. These diameters were measured according to techniques known in the art: a standard size curve was constructed by analysis of beads of defined diameters (Molecular Probes, Eugene, Oreg.), whereby their forward light scatter channel signs were measured. Keeping all instrument settings constant, the mean channel forward light scatter of the CD34$^+$ cell fractions were obtained, and were plotted on the standard curve to obtain a mean cell diameter for the population. These results were confirmed by use of art-accepted nomogram determination of cell size.

The distribution of cells in the CE-sized fractions before and after treatment with soybean agglutinin and selection for CD34 is set forth in Table 1.

TABLE 1

Percentage of Bone Marrow Mononuclear Cells in Fraction

| FR | Percentage |
|---|---|
| R/O (total) | 61 |
| 33 (total) | 26 |
| 25 (total) | 11 |
| R/O CD34$^+$ | 1.00 |
| 33 CD34$^+$ | 0.20 |
| 25 CD34$^+$ | 0.06 |

As shown in Table 1, about 1% of the original number of the unfractionated cells were recovered in all of the three CD34$^+$ fractions. After CE, about $\frac{1}{9}$th of the low density mononucleated cells were recovered in FR $^{25}/_{29}$, about ¼th in Fr $^{33}/_{37}$ and about half in the R/O fraction. Soybean agglutinin (SBA) depletion results in the loss of 70–90% of cells treated for all fractions, and about 3–5% of the SBA cells are recovered by the CD34 positive selection. About 25–55% of the CD34$^+$ cells in the LD mononuclear bone marrow fraction are recovered by this methodology.

The morphology of the CD34$^+$ cells varies between the three fractions. The CD34$^+$ cells recovered from FR $^{25}/_{29}$ were small, lymphoid appearing cells with scant agranular cytoplasm and 0–1 nucleoli. CD34$^+$ cells from FR $^{33}/_{37}$ were slightly larger, lymphoblast-like cells with scant agranular cytoplasm and 1–5 nucleoli. CD34$^+$ cells from the R/O fraction were significantly larger myelo/erythroblasts with few nucleoli and frequently a significant amount of cytoplasm containing granules. These results were confirmed by horizontal and vertical light scatter as shown in Figures 1A–1D. The X-axis measures horizontal side scatter and is a measure of cell granularity. The Y-axis measures forward light scatter and is a measure of cell size. FIG. 1A shows the original population distribution, FIG. 1B shows the R/O fraction, FIG. 1C, FR $^{25}/_{29}$ and FIG. 1D, FR $^{33}/_{37}$. The mean diameter of the FR R/O CD34$^+$ cell fraction was 13.5 μm; that of the FR $^{33}/_{37}$ CD34$^+$ cell fraction was 9.3 μm and that of the FR $^{25}/_{29}$CD34$^+$ fraction was 8.5 μm.

EXAMPLE 2

Phenotypic Markers of Fractionated Cells

Upon phenotype analysis, ≧85% of the cells were recognized by 8G12. Unfractionated cells and each cell fraction were individually preincubated with 0.5% Gammimune and then washed with phosphate-buffered saline (PBS, Gibco) containing 0.1% sodium azide (Sigma Chemical Co.). Phycoerythrin-conjugated anti-CD2, CD19, CD33, CD38 or anti-HLA-DR (Becton Dickinson, Sunnyvale, Calif.) was added to the cell pellet and incubated for 30 minutes at 4° C. The cells were washed twice with PBS-azide and resuspended in 1% paraformaldehyde (Electron Microscopy Science) for analysis within one week. The cells were analyzed on a FACS Star Plus (Becton Dickinson) interfaced to a VACS computer using Becton Dickinson Concert 40 software. Positive binding was defined as fluorescence on antibody-reacted cells beyond that on control cells.

The results are shown in Table 2.

TABLE 2

| FRAC-TION | SURFACE ANTIGEN ANALYSIS* | | | | |
|---|---|---|---|---|---|
| | % CD2$^+$ | % CD19$^+$ | % CD33$^+$ | % CD38$^+$ | HLA-DR$^+$ |
| UNS | 7 ± 3 | 7 ± 3 | 7 ± 5 | 2 ± 2 | 9 ± 1 |
| FR 25/29 | 7 ± 3 | 3 ± 1 | 0 ± 0 | 4 ± 1 | 2 ± 1 |
| FR 25/29 CD34$^+$ | 30 ± 0 | 0 ± 0 | 0 ± 0 | 9 ± 2 | 18 ± 4 |
| FR 33/27 | 7 ± 2 | 8 ± 1 | 1 ± 0 | 17 ± 3 | 5 ± 2 |
| FR 33/37 CD34$^+$ | 0 ± 2 | 13 ± 7 | 3 ± 2 | 33 ± 10 | 39 ± 10 |
| R/O | 0 ± 2 | 4 ± 1 | 21 ± 4 | 39 ± 14 | 15 ± 3 |
| R/O CD34$^+$ | 0 ± 2 | 4 ± 1 | 62 ± 11 | 83 ± 2 | 80 ± 3 |

*Mean and standard deviation for 7 experiments.

While the majority of the CD34$^+$ cells in the R/O fraction expressed CD38 and HLA-DR and to a slightly lesser extent CD33, few if any of the cells expressed CD2 or CD19. Most of the CD34$^+$ cells in FR $^{25}/_{29}$ did not express CD19, CD33, CD38 or HLA-DR but did express about 30% CD2 (range 21–40% in 4 experiments). The frequency of CD34$^+$ cells from FR $^{33}/_{37}$ expressing CD38 and HLA-DR falls in between the other fractions with about 40% of the cells expressing CD38 and HLA-DR. Of the CD19$^+$/CD34$^+$cells, the majority are recovered in FR $^{33}/_{37}$.

EXAMPLE 3

Assay for Progenitors

A portion of each fraction was cultured with 1.32% methylcellulose (1,500 CP, Sigma), 30% FBS (Hyclone Laboratories Inc., Logan, Utah), 5×10-4 mol/L 2-mercaptoethanol, 5% phytohemagglutinin-leucocyte conditioned medium (PHA-LCB), 1% BSA, 10-6 mol/L of methylprednisolone sodium succinate ester, and 1 U/ml of recombinant human erythropoietin (Amgen, Thousand Oaks, Calif.). Cultures were seeded in triplicate at 1×10$^3$ and 1×10$^5$ cells/ml in 1 ml culture dishes (Nunc) and maintained in humidified atmosphere at 37° C. in 5% CO$_2$. The plates were scored for BFU-E and CFU-GM at day 14 using an inverted microscope. These results are shown in Table 3.

TABLE 3

| | FREQUENCY* | | |
|---|---|---|---|
| FRACTION | CFU-GM/10$^5$ | BFU-E/10$^5$ | ENRICHMENT |
| UNS | 185 ± 23 | 113 ± 10 | — |
| FR 25/39 | 0 ± 0 | 0 ± 0 | 0.0 |
| FR 25/39 CD34$^+$ | 6 ± 1 | 14 ± 1 | 0.1 |
| FR 33/37 | 4 ± 2 | 16 ± 6 | 0.1 |

TABLE 3-continued

| | FREQUENCY* | | |
|---|---|---|---|
| FRACTION | CFU-GM/$10^5$ | BFU-E/$10^5$ | ENRICHMENT |
| FR 33/37 CD34$^+$ | 248 ± 27 | 142 ± 46 | 1.3 |
| R/O | 170 ± 13 | 410 ± 98 | 1.9 |
| R/O CD34$^+$ | 3220 ± 420 | 5300 ± 512 | 28.0 |

*Mean and standard deviation for 7 experiments.

There was no marked enrichment of colony-forming cells (CFU-GM, CFU-GEMM or BFU-E) in any fraction after elutriation, but the R/O CD34$^+$ subpopulation was 20–59 fold enriched in these colony-forming cells. FR $25/29$ CD34$^+$ produced no CFU-GM, BFU-E or CFU-GEMM.

EXAMPLE 4

Long-Term Bone Marrow Culture

Normal allogeneic stromal layers were cultured in T25 flasks (Corning Glass Works, Corning, N.Y.) for 14–28 days and then irradiated at 1000 cGy with a MARK I Cesium irradiator (Shepard and Associates, Glendale, Calif.). Five to seven days after irradiation, cells from each CD34$^+$ fraction ($10^5$ to $10^6$) in 5 mL McCoy's 5A medium with 12.5% FCS, 12.5% horse serum (Hyclone Laboratories), 2 mM L-glutamine, 0.07% sodium bicarbonate solution, 1% (v/v) MEM nonessential amino acid solution, 1% (v/v) MEM vitamin solution, 1% (v/v) sodium pyruvate solution, 1000 units/mL penicillin, 100 units/mL streptomycin, and $10^{-7}$ hydrocortisone (A-Hydrocort, Abbott Laboratories, Chicago, Ill.) were seeded into each flask. Cultures were maintained in humidified atmosphere at 37° C. in 5% $CO_2$. At weekly intervals the cultures were fed by removing half of the supernatant and replacing it with fresh media. Nonadherent cells were counted and assayed for the presence of CFU-GM and BFU-E in methylcellulose assay on weeks 0, 2, 5, 6, 7 and 8.

Figure 2:
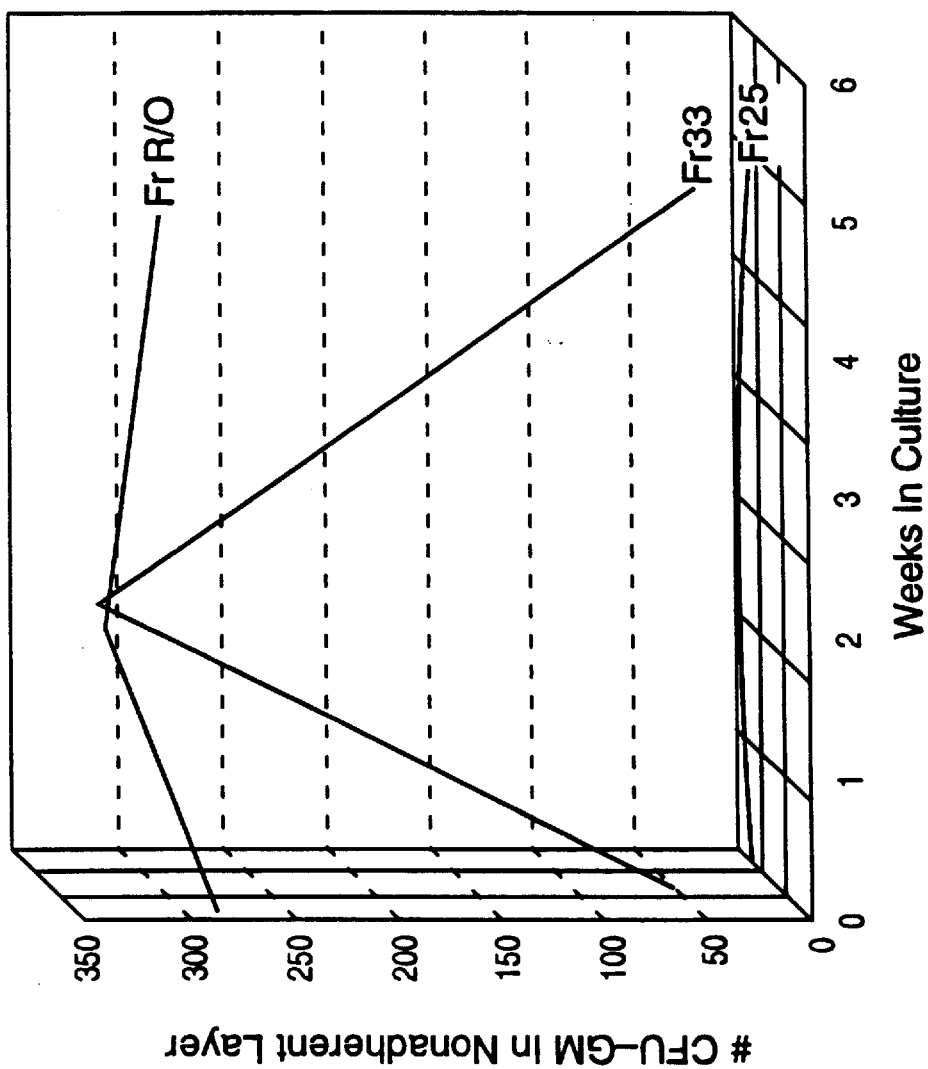
FIG. 2 is a graph showing CFU-GM from various CD34$^+$ fractions.
Figure 3:
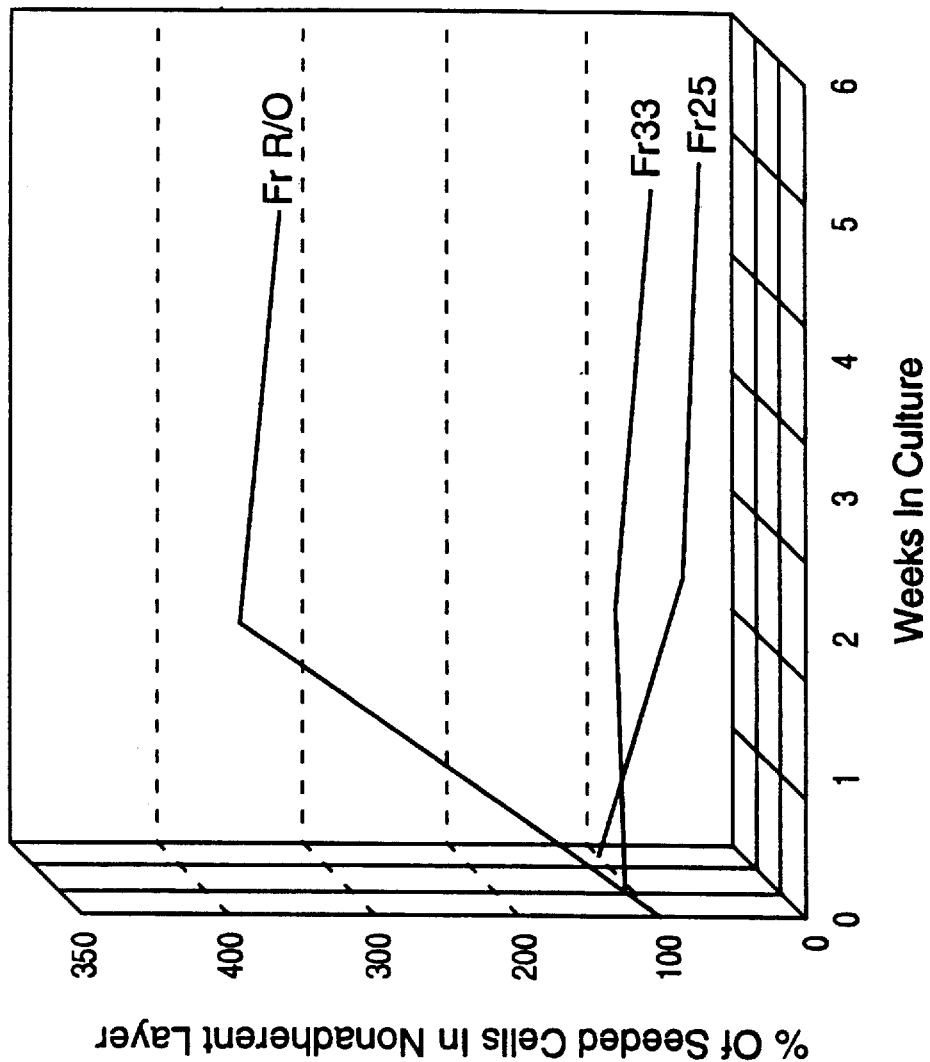
FIG. 3 is a graph showing proliferation of various CD34$^+$ fractions.

The results for CFU-GM are shown in FIG. 2. There were increases and/or sustenance in the total number of cells in the nonadherent layer at several time points for cultures initiated with either FR $33/37$ or R/O CD34$^+$ cells. Similarly, clonogenic cells were recovered from both FR $33/37$ and R/O CD34$^+$ cells as late as week 8. However, in 4 experiments, few nucleated cells and no CFU-GM, BFU-E or CFU-GEMM were ever recovered from the nonadherent layer of long-term bone marrow cultures seeded with FR $25/29$ CD34$^+$ cells (FIGS. 2 and 3). This indicates the very primitive nature of this CD34$^+$ cell and can contrast it with other subpopulations of CD34$^+$ cells which do proliferate in long-term bone marrow culture.

EXAMPLE 5

Assay for Cytokine Receptors

Cells from each CD34$^+$ fraction were assayed for the presence of receptors for Steel factor (SCF), granulocyte-macrophage colony stimulating factor (GM-CSF), granulocyte colony stimulating factor (G-CSF), interleukin-1 (IL-1), IL-2, IL-3, IL-6, macrophage inhibitory protein MIP1α. Samples were washed twice in Hepes-buffered saline (150 mM NaCl, 25 mM hepes, ph 7.4) and then incubated with 100 ng biotinylated rhSCF (R&D Systems, Minneapolis, Minn.) for 60 min on ice. Afterwards, cells were washed twice in 2 mL RDF1 wash buffer (R&D Systems) and then incubated with 100 ng avidincarboxyfluorescein (R&D Systems) for 30 min on ice in the dark. The cells were washed with 2 mL RDF1 buffer and resuspended in 300 uL of Hepes-buffered saline for flow cytometric analysis.

Stained cell samples were analyzed for fluorescent intensity on either the EPICS Profile II or Epics 752 flow cytometer (Coulter Electronics, Hialeah, Fla.). Positive samples were compared to samples stained with avidincarboxyfluorescein alone. Specificity of the biotinylated cytokine was confirmed by complete inhibition or binding in the presence of a 10 molar-fold excess of unlabelled cytokine. The results are shown in Table 4.

TABLE 4

| | CYTOKINE RECEPTOR ANALYSIS* | | | | | |
|---|---|---|---|---|---|---|
| FRACTION | % SCFr$^+$ | % IL-6r$^+$ | % IL-3r$^+$ | % GM-CSFr$^+$ | % G-CSFr$^+$ | % IL-1r |
| FR $25/29$ CD34$^+$ | 74 ± 10 | 64 ± 9 | 53 ± 11 | 62 ± 8 | 39 ± 18 | 85 ± 2 |
| FR $33/37$ CD34$^+$ | 66 ± 13 | 39 ± 39 | 18 ± 8 | 33 ± 28 | 12 ± 6 | 64 ± 35 |
| R/O CD34$^+$ | 64 ± 18 | 30 ± 26 | 7 ± 2 | 20 ± 26 | 13 ± 2 | 67 ± 29 |

*Mean and standard deviation of 7 experiments.

Virtually all (>90%) the CD34$^+$ cells expressed receptors for SCF, but the intensity of fluorescence was greatest for FR $25/29$ CD34$^+$ cells. Bright and dim populations of cells were routinely observed in this fraction. Only single populations of cells were noted for FR $33/37$ and R/O CD34$^+$ cells with the R/O CD34$^+$ subpopulation having only dim cells.

Virtually all the CD34$^+$ cells had receptors for MIP1α, but FR $25/29$ CD34$^+$ cells exhibited the greatest number of receptors. The R/O CD34$^+$ cells exhibited the least number of receptors.

Receptors for IL-1, IL-3, I1-6, GM-CSF and G-CSF were found on all subpopulations of CD34$^+$ cells. Comparing the 3 fractions, receptors for IL-3, IL-6 and GM-CSF were highest on FR $25/29$ CD34$^+$ cells.

By analysis of this receptor profile appropriate culture protocols for these cells are devised.

We claim:

1. A population of quiescent human hematopoietic stem cells consisting essentially of agranular, mononuclear hematopoietic cells which are CD34$^+$, wherein said population is characterized in that it:
    (a) fails to produce substantial numbers of CFU-GM or BFU-E after 14 days in methyl cellulose culture, and
    (b) is obtainable by a process which comprises
        (i) subjecting hematopoietic low-density mononuclear cells to size separation to obtain a first size-fractionated subpopulation of cells having a size equivalent to cell fractions obtained at a flow rate of 25–29 ml/min in counterflow elutriation performed at 900×g;
        (ii) optionally contacting said first subpopulation with soybean agglutinin immobilized to a solid support and recovering a second subpopulation of cells which are nonadherent to said immobilized soybean agglutinin;

(iii) contacting said first or said second subpopulation with an affinity ligand for CD34 immobilized to a solid support; and (iv) recovering cells adherent to said immobilized CD34 ligand, thereby obtaining said quiescent hematopoietic stem cell population.

2. A method of delivering quiescent human hematopoietic stem cells into a subject in need of said cells, comprising transplanting into said subject, cells of the quiescent human hematopoietic stem cell population of claim 1.

3. The method of claim 2 wherein said cells have been genetically altered.

4. A method to prepare a population of quiescent human hematopoietic stem cells which comprises (a) subjecting hematopoietic low-density mononuclear cells to size separation to obtain a first size-fractionated subpopulation of cells having a size equivalent to cell fractions obtained at a flow rate of 25–29 ml/min in counterflow elutriation at 900×g;

(b) contacting said first subpopulation with an affinity ligand for CD34 which is immobilized to a solid support; and (c) recovering cells adherent to said solid support thereby preparing said quiescent hematopoietic stem cell population.

5. The method of claim 4 wherein said hematopoietic cells are obtained from bone marrow.

6. The hematopoietic quiescent stem cell population of claim 1 which has been prepared by a method which comprises:

(a) subjecting hematopoietic low-density mononuclear cells to counterflow elutriation and recovering a first size-fractionated cell subpopulation at the flow rate of 25–29 ml/min and a relative centrifugal force of 900×g;

(b) optionally contacting said first subpopulation with soybean agglutinin immobilized to a solid support and recovering a second subpopulation of cells which are nonadherent to said immobilized soybean agglutinin (c) contacting said first or said second subpopulation with an affinity ligand for CD34 immobilized to a solid support; and (d) recovering cells adherent to said immobilized CD34 ligand, thereby obtaining said quiescent hematopoietic stem cell population.

7. A population of quiescent human hematopoietic stem cells consisting essentially of agranular, mononuclear hematopoietic cells which (a) are $CD34^+$, (b) fail to produce substantial numbers of CFUGM or BFU-E after 14 days in methyl cellulose culture, and (c) correspond in size to cells obtained at a flow rate 25–29 ml/min in a counterflow centrifugal elutriation performed at a relative centrifugal force of 900×g.

8. A method to prepare a population of quiescent human hematopoietic stem cells which comprises (a) subjecting hematopoietic low-density mononuclear cells to size separation to obtain a first size-fractionated subpopulation of cells having a size equivalent to cell fractions obtained at a flow rate of 25–29 ml/min in counterflow elutriation at 900×g;

(b) contacting said first subpopulation of cells with soybean agglutinin immobilized to a solid support and recovering a second subpopulation of cells which are nonadherent to said soybean agglutinin;

(c) contacting said second subpopulation of cells with an affinity ligand for CD34 which is immobilized to a solid support; and (d) recovering cells adherent to said affinity ligand for CD34, thereby preparing said quiescent hematopoietic stem cell population.

* * * * *